(12) United States Patent
Guidry et al.

(10) Patent No.: US 6,984,381 B2
(45) Date of Patent: Jan. 10, 2006

(54) VACCINE FOR THE PREVENTION OF BACTERIAL INFECTION OF THE BOVINE MAMMARY GLAND

(75) Inventors: Albert Guidry, Nellysford, VA (US); Celia O'Brien, Ellicott City, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/189,251

(22) Filed: Jul. 5, 2002

(65) Prior Publication Data

US 2004/0028688 A1   Feb. 12, 2004

(51) Int. Cl.
*A01N 63/00* (2006.01)
*A61K 39/02* (2006.01)
*A61K 39/085* (2006.01)
*A61K 39/38* (2006.01)

(52) U.S. Cl. .............................. 424/93.42; 424/243.1; 424/237.1; 424/234.1; 424/184.1; 424/831; 424/823; 424/824; 424/825

(58) Field of Classification Search ............. 424/93.42, 424/93.1, 234.1, 237.1, 263.1, 186.1, 197.11, 424/831, 813, 823–825

See application file for complete search history.

(56) References Cited

U.S. PATENT DOCUMENTS

| | | | |
|---|---|---|---|
| 4,197,290 A | 4/1980 | Yoshida | 424/92 |
| 4,327,082 A | 4/1982 | Armitage | 424/92 |
| 4,425,330 A | 1/1984 | Norcross et al. | 424/92 |
| 4,748,020 A | 5/1988 | von Malsen-Ponickau | 424/92 |
| 4,762,712 A | 8/1988 | Stolle et al. | 424/92 |
| 5,032,522 A | 7/1991 | Watson | 435/252.1 |
| 5,198,214 A | 3/1993 | Stolle et al. | 424/92 |
| 5,571,514 A | 11/1996 | Hook et al. | 424/190.1 |
| 5,679,349 A | 10/1997 | Scheifinger et al. | 424/349 |
| 5,770,208 A | 6/1998 | Fattom et al. | 424/197.11 |
| 5,980,908 A | 11/1999 | Hook et al. | 424/243.1 |
| 6,194,161 B1 | 2/2001 | Fattom et al. | 435/7.1 |
| 6,291,431 B1 | 9/2001 | Balaban et al. | 514/16 |
| 6,294,177 B1 | 9/2001 | Fattom | 424/243.1 |

FOREIGN PATENT DOCUMENTS

WO   WO 98/10788   * 3/1998

OTHER PUBLICATIONS

R. A. Almeida et al., "*Staphylococcus aureus* Invasion of Bovine Mammary Epithelial Cells", *J. Dairy Sci.*, vol. 79, (6) pp. 1021-1026, 1996.

E. Cifrian et al., "Adherence of *Staphylococcus aureus* to Cultured Bovine Mammary Epithelial Cells[1]", *J. Dairy Sci.*, vol. 77, (4) pp. 970-983, 1994.

A. Guidry et al., "Serotyping scheme for *Staphylococcus aureus* isolated from cows with mastitis", *AJVR*, vol. 59, (12), pp. 1537-1540, Dec. 1998.

A. Guidry et al., "Prevalence of capsular serotypes among *Staphylococcus aureus* isolates from cows with mastitis in the United States", *Veterinary Microbiology*, vol. 59, pp. 53-58, 1997.

C. N. O'Brien et al., "Immunization with *Staphylococcus aureus* Lysate Incorporated into Microspheres[1]", *J. Dairy Sci.*, vol. 84, (8), pp. 1791-1799, 2001.

C. N. O'Brien et al., "Production of Antibodies to *Staphylococcus aureus* Serotypes 5, 8, and 336 Using Poly (DL-Lactide-CO-Glycolide) Microspheres[1]", *J. Dairy Sci.*, vol. 83, (8),pp. 1758-1766, 2000.

T. Tollersrud et al., "Genetic and Serologic Evaluation of Capsule Production by Bovine Mammary Isolates of *Staphylococcus aureus* and other *Staphylococcus* spp. from Europe and the United States", *Journal of Clinical Microbiology*, vol. 38 (8), pp. 2998-3003, Aug. 2000.

* cited by examiner

Primary Examiner—S. Devi
(74) Attorney, Agent, or Firm—John D. Fado; Evelyn M. Rabin

(57) ABSTRACT

A novel vaccine for immunizing animals against *Staphylococcus aureus*-induced mastitis is disclosed. The vaccine is comprised of whole killed cells of *S. aureus* in a dosage effective to immunize an animal against the organism, in combination with a pharmaceutically acceptable carrier.

7 Claims, No Drawings

VACCINE FOR THE PREVENTION OF BACTERIAL INFECTION OF THE BOVINE MAMMARY GLAND

BACKGROUND OF THE INVENTION

1. Field of the Invention

This invention relates to a novel vaccine specific for *Staphylococcus aureus*, the major bacterium responsible for bovine mastitis. The strains of the invention are used in vaccine development, to protect individuals from *S. aureus* infection and to treat and control *S. aureus*-induced mastitis.

2. Description of the Relevant Art

*S. aureus* mastitis affects 90% of US. Dairy herds. Annual loss due to mastitis in the United States is two billion dollars (Nickerson et al. 1984. *J. Dairy Res.* 51: 209–217). Antibiotic treatment of *S. aureus* infections has met with limited success due to the development of antibiotic resistant strains and their ability to survive within polymorphonuclear neutrophils (PMN) and macrophages where very few antibiotics achieve effective intracellular concentrations (Craven and Anderson. 1984. *J. Dairy Res.* 51:513–523). *S. aureus* mastitis is rarely acute, but causes subclinical, chronic infections (Bramley and Dodd. 1984. *J. Dairy Res.* 51:481–512). Cows are most susceptible to *S. aureus* infections during the transition from lactation to involution and from involution to colostrogenesis (Oliver and Sordillo. 1988. *J. Dairy Sci.* 71: 2584–2606). The bovine udder has numerous defense mechanisms to protect against invading pathogens.

The first line of defense against bacterial invasion of the udder is the smooth muscle sphincter surrounding the teat end (Frost, A. J. 1990. In: *Proc. Int. Symp. Bovine Mastitis*, Page 1) and keratin, a waxy material found in the teat canal (Murphy, J. M. 1959. *Cornell Vet.* 49: 411–421). However, bacteria can breach the teat canal and enter the gland cistern by multiplication or reverse flow during milking machine pulsation (Nickerson, S. C. 1986. In: *Dairy Research Report*, Louisiana Agric. Experiment Station, Page 211; Schalm et al. 1971. In: *Bovine Mastitis*, Lea and Febiger, Philadelphia, Pa., Page 209).

Once inside the gland, the second line of defense against invading pathogens is phagocytosis by neutrophils and macrophages. Macrophages are the predominant cell type in uninfected lactating glands, but neutrophils are recognized as the most important phagocytic cell because of their rapid migration from blood during an intramammary infection and because of their efficient phagocytosis of bacteria (Paape et al. 1979. *J. Dairy Sci.* 62: 135–153). Neutrophils migrate from blood to milk in response to chemoattractants produced by bacteria and the host during the inflammatory process. Once inside the gland cistern, neutrophils must rely on random collisions to bring them into contact with invading organisms. Large numbers of neutrophils ($9\times10^5$ neutrophils/ml) are required to provide effective protection. However, this concentration far exceeds the number of neutrophils actually found in the healthy gland ($<1\times10^5$ neutrophils/ml).

However, phagocytosis by neutrophils and macrophages present in the milk can be enhanced by specific antibodies (immunoglobulins (Ig), opsonins) which act to reduce the number of neutrophils needed to resist infection. Antibodies bind to bacteria via the Fab region of the Ig. Neutrophils attach to bacteria via surface receptors for the Fc portion of Ig and ingest the bacteria. Such bacterial attachment via Fc receptors promotes both ingestion and digestion of the organism. Bovine neutrophils have Fc receptors for $IgG_2$ and bovine mammary macrophages have Fc receptors for $IgG_1$. However, once inside the gland, *S. aureus* form an exopolysaccharide capsule that is itself low in immunogenicity and also serves to block Ig Fab from recognizing the highly antigenic cell-wall proteins it encapsulates. Thus, stimulation of the production of specific opsonins to *S. aureus* is inhibited by this formation of an exopolysaccharide capsule, a fact having a distinct bearing on the composition required for a vaccine against *S. aureus*.

Once ingested, bacteria are contained in a vacuole (phagosome). Phagosomes fuse with lysosomal granules to form phagolysosomes which together contain oxygen-dependent and oxygen-independent antibacterial mechanisms and enzymes that kill and digest the organisms. Unfortunately, phagocytosis and killing of *S. aureus* is not always complete (Craven et al. 1984. *J. Dairy Res.* 51: 513–523) and the *S. aureus* that survive are capable of multiplication, increasing the chances for establishing chronic infections. However, phagocytized *S. aureus* are flushed out during milking.

Should the *S. aureus* escape phagocytosis, they have the potential to adhere to the epithelial lining of the gland, the first step in the colonization in the udder (Frost, A. J. 1975. *Infect. Immun.* 12:1154–1156; Wanasinghe, D. D. 1981. *Acta Vet Scand.* 22: 109–117). Growth in milk increases the ability of *S. aureus* to adhere to epithelial cells (Mamo et al. 1994. *Microbiol. Immunol.* 38: 305–308). Organisms adhere to the epithelium lining the gland cistern and milk ducts and form small colonies that become covered with an exopolysaccharide capsule (Nickerson, S. C. 1993. In: *Proc. Reg. Meeting Natl. Mastitis Council*, Syracuse, N.Y., Page 64). Toxins produced by adhered *S. aureus* damage the underlying epithelium. Eventually, *S. aureus* penetrate the epithelium and establish deep-seated abscesses that become walled off by scar tissue. These abscesses are impenetrable by antibiotics and therefore result in chronic subclinical infections (Guterbock, W. M. 1992. *Vet Med.* X: 1229–1234).

Different mastitis pathogens have different target cell specificities and use different mechanisms to adhere to cells of the bovine mammary gland (Lammers et al. 2001. *Vet. Microbio.* 80(3): 255–265). The mechanism(s) for *S. aureus* adherence to epithelial cells is not clearly understood, but the host receptors collagen and fibronectin have been identified (Cifrian et al. 1994. *J. Dairy Sci.* 77: 970–983; Cifrian et al. 1996. *Vet. Microbiol.* 48: 187–198; Cifrian et al. *Am. J. Vet. Res.* 57: 1308–1311; Dziewanowska et al. 1999. *Infect. Immun.* 67: 4673–4678; Foster, T. J. 1991. *Vaccine* 9: 221–227; Foster and Hook. 1998. *Trends in Microbiol.* 6: 484–488; Hensen et al. 2000. *J. Dairy Sci.* 83: 418–429; Joh et al. 1994. *Biochem.* 33: 6086–6092; Joh et al. 1999. *Matrix Biol.* 18: 211–223; Mohamed et al. 1999. *Infect. Immun.* 67: 589–594). Fibronectin-binding proteins are present on the cell wall of the majority of *S. aureus* isolates and appear to be a major player in bacterial adherence (Lammers et al. 1999. *FEMS Microbiol. LETT.* 180: 103–109). However, the exact mechanism of fibronectin adherence has not been defined (Joh et al., 1999, supra). In addition to facilitating adherence, this interaction has been shown to induce a host protein that inhibits phagocytosis (Jonsson and Wadstrom. 1993. In: *Pathogenesis of Bacterial Infections in Animals*, Gyles and Thoen, Eds., Iowa State University Press, Ames, Iowa, Page 21). Recent studies demonstrated that specific antibody to staphylococcal fibronectin-binding protein blocked tissue adherence and enhanced phagocytosis (Mamo et al. 1995. *Microb. Pathog.* 19: 49–55; Cifrian et al. 1994. *J. Dairy Sci.* 77: 970–983). *S. aureus* have also been shown to bind to collagen and laminin (Cifrain et al. 1996,

*Am. J. Vet Res.*, supra) which can also be blocked by specific antibodies (Lorca et al. 2002. *FEMS Microbiol. Lett* 206: 31–37).

Attempts have been made to produce antibodies which are specific for *S. aureus* and which will enhance phagocytosis. Such attempts have focused on the changing surface properties of the organisms once inside the gland (Aguilar et al. 2001. *Vet. Microbiol.* 82(2): 165–175; Lorca et al., supra; Nickerson et al., 1993, supra. Norcross et al. 1983. Nordhaug et al. *J. Dairy Sci.* 77: 1267–1275; Nordhaug et al. *J. Dairy Sci.* 77: 1276–1284; Olmsted et al. 1992. *Infect. Immun.* 60: 249–256). Though *S. aureus* form an exopolysaccharide capsule upon entering the mammary gland, there is a period of time during the logarithmic growth phase that *S. aureus* are unencapsulated, thus exposing the highly antigenic cell-wall proteins. Adherence proteins are among the cell-wall proteins, which makes this a critical phase in the *S. aureus* invasion of the gland. This is the phase during which both opsonizing and anti-adherent antibodies are most effective. Upon reaching the stationary phase of the growth cycle in vivo, *S. aureus* produce an exopolysaccharide capsule. The exopolysaccharide capsule is low in imunogenicity; and furthermore, there are multiple capsule serotypes, thus increasing the difficulty of generating opsonizing antibodies.

Numerous attempts have been made to produce vaccines that induce protective antibodies against *S. aureus*. These attempts have met with varying degrees of success. These have included whole cell, cell lysates, toxoids, live attenuated organisms, and inactivated organisms (Brock et al. 1975. *Res. Vet Sci.* 19: 152–158; Buzzola et al. 2001. *Epidemiol. Infect.* 126(3): 445–452; Calzolare et al. 1997. *J. Dairy Sci.* 80: 854–858; Derosa et al. 1997. *Zentralbl. Veterinarmed.* [B] 44: 599–607; Giraudo et al. 1997. *J. Dairy Sci.* 80: 845–853; Herbelin et al. 1997. *J. Dairy Sci.* 80: 2025–2034; O'Brien et al. 2000. *J. Dairy Sci.* 83:1758–1766; O'Brien et al. 2001. *J. Dairy Sci.* 84: 1791–1799; Tyler et al. 1993. *Vet. Clin. North Am. Food Anim. Pract.* 9: 537–549; Watson, D. L. 1984. J. Dairy Sci. 67: 2608–2613; Watson, D. L. 1992. *Res. Vet. Sci.* 53: 346–353; Watson et al. 1996. *Aust. Vet. J.* 74: 447–450; Yoshida et al. 1984. *J. Dairy Sci.* 67: 620–627; Zecconi et al. 1999. *J. Dairy Sci.* 82: 2101–2107). Varying serotypes have been a major factor in the limited success of these vaccines (Hensen et al., supra; Sordelli et al. 2000. *J. Clin. Microbiol.* 38: 846–850; Tollersrud et al. 2000. J. Clin. Microbiol. 38: 2998–3003). The importance of using the appropriate serotype in producing a *S. aureus* vaccine is evident by the improved success of vaccines prepared from individual herd isolates (autogenous vaccines; Hwang et al. 2000. J. Vet Med. Sci. 62: 875–880; Sears et al. 1999. Natl. Mastitis Council Annual Meeting, National Mastitis Council, Inc., Pages 86–92). Where autogenous vaccines have failed could be attributed to variation of serotypes within a herd (Guidry et al. 1997. *Vet Microbiol.* 59: 53–58; Hoedemaker et al. 2001. *J. Vet Med. B Infect. Dis. Vet Public Health* 48: 373–383).

Thus, there is a need for agents useful for the immunotherapy of *S. aureus*-induced mastitis which would prevent or limit the disease.

SUMMARY OF THE INVENTION

We have identified a particular combination of *S. aureus* strains expressing specific antigens which can be used in vaccine development to prevent or treat *S. aureus*-induced mastitis in animals, particularly bovine animals.

In accordance with this discovery, it is an object of the invention to provide a mixture of whole cells from the particular combination of *S. aureus* strains and to use the combination in a method to elicit an immune response specific for *S. aureus*.

It is also an object of the invention to generate monoclonal or polyclonal antibodies for use in immuno-therapeutic methods for preventing and treating *S. aureus*-induced mastitis.

Another object of the invention relates to a method of inhibiting or ameliorating a *S. aureus*-induced mastitis infection in an individual comprising administering to an individual in need of such treatment a particular combination of *S. aureus* antigens in an amount effective to prevent or decrease the severity of *S. aureus*-induced mastitis.

An added object of the invention is to provide compositions and methods useful for protecting animals against *S. aureus*-induced mastitis.

Also part of this invention is a *S. aureus*/mastitis kit, comprising a mixture of particular strains of *S. aureus*; and instructions for the use of the kit.

Other objects and advantages of this invention will become readily apparent from the ensuing description.

DETAILED DESCRIPTION OF THE INVENTION

The present invention provides a vaccine comprised of a mixture of killed whole cells from a particular combination of *S. aureus* strains, the combination having been found to both protect and to ameliorate bovine mastitis, a method of producing that vaccine and a method of using the vaccine to protect individuals from mastitis and to ameliorate the disease.

A serotyping system for *S. aureus* capsule antigens was developed by Karakawa and Vann and consists of eight serotypes (1982. In: *Seminars in Infectious Diseases*, Bacterial Vaccines, Vol. IV, Weinstein et al, Eds., Thieme-Stratton, NY, Pages 285–293). Poutrel et al. have reported on the prevalence of capsular polysaccharide Types 5 and 8 among *S. aureus* isolates from cow, goat, and ewe milk in France. In their study, the primary serotypes found were Types 5 (51%) and 8 (18%); 31% were non-typeable (1988. *J. Clin. Microbiol.* 26: 38–40). In an attempt to produce a universal *S. aureus* vaccine, our laboratory surveyed dairy herds in the major milk producing areas of the United States through the cooperation of the state diagnostic laboratories in the major dairy producing states. We characterized *S. aureus* serotypes isolated from cases of bovine mastitis obtained from veterinary diagnostic laboratories that service 44% of the dairy cattle in the United States (Guidry et al., 1997, supra). In our studies, serotype 5 accounted for 18% of the isolates and serotype 8 for 23%; however, 59% of the isolates were not typeable with either Type 5 or 8 antisera. This survey revealed that three serotypes accounted for 100% of the *S. aureus* isolated from cases of mastitis in dairy cattle. A similar survey revealed that these three serotypes accounted for 95% of the *S. aureus* isolated from cases of bovine mastitis in Korea (Han et al. 2000. *J. Vet Med. Sci.* 62: 1331–1333). Later studies (Guidry et al. 1998. *Am. J. Vet. Res.* 59:1537–1539) confirmed that all strains not typeable with either Type 5 or Type 8 antisera were found to be Type 336 by use of direct cell agglutination and immunoprecipitation of cell extracts with antiserum 336. The current vaccine is composed of representatives of each of these three serotypes. The vaccine of this invention is effective for controlling Staphylococcal infections in a variety of animals when administered thereto. Without being limited thereto, the vaccine is especially beneficial for the treatment of ruminants, particularly bovine, sheep, and goats. To our knowledge there is no comparable vaccine available.

Fattom (2001. U.S. Pat. No. 6,294,177) typed human clinical isolates obtained from various sources and reported that approximately 60% of human isolates were Type 8, approximately 30% were Type 5, and nearly all of the remaining 10% were Type 336. Fattom further obtained an additional 27 human isolates that were not typeable as either Type 5 or Type 8 and determined that they too were typeable as Type 336. Utilizing a representative strain of S. aureus isolated from human clinical samples, a strain that carries the 336 antigen and that has been deposited with the ATCC as accession number 55804, Fattom reported that 28.4% of 102 bovine mastitis isolates from Europe were Type 336 and 61.6% of bovine mastitis isolates from the United States were 336 positive. U.S. Pat. No. 6,294,177 (Fattom) describes a vaccine that comprises cells, cell lysates, or cell derivatives which have the characteristic of specifically binding with antibodies to S. aureus Type 336 deposited under ATCC 55804 and a vaccine which additionally comprises cells, cell lysates, or cell derivatives of S. aureus which carry Type 5 antigen and cells, cell lysates, or cell derivative of S. aureus which carry Type 8 antigen. However, in the Fattom studies, treatment and prevention of veterinary S. aureus infections with the '177 vaccines comprising ATCC 55804-based Type 336 were not reported.

The present invention relates to our strategy for generating an effective vaccine for preventing and treating veterinary S. aureus infections; namely, that the vaccine comprise capsule antigens and, importantly, adherence antigens. As described above, cell wall antigens of S. aureus are involved in adherence to epithelial cells. Adherence is followed by encapsulation and toxin production. The majority of unencapsulated strains of S. aureus express the 336 antigen as detected by direct cell agglutination. Capsulated strains of S. aureus also express the 336 antigen on their cell wall; however, different growth conditions are required for detection of the 336 antigen on capsulated strains because the capsule impedes the agglutination reaction. These facts, taken together, indicate that most S. aureus strains, whether capsulated or unencapsulated, can be shown to be positive for the 336 cell wall antigen when grown under conditions where expression of cell wall antigens can be detected.

Strains identified as unencapsulated strains are usually found to have the characteristic of adhering to epithelial cells. Interestingly, the unencapsulated S. aureus isolate identified as ATCC 55804 and typed as 336 positive exhibits little adherence to bovine mammary epithelial cells. However, the present invention teaches a trivalent whole cell vaccine comprising cells of strains expressing Type 5 and Type 8 capsular antigens and cells of a 336 positive unencapsulated S. aureus strain which is adherent, i.e., Smith Compact, deposited at the American Type Culture Collection, ATCC, 10801 University Blvd., Manassas, Va. 20110 on Mar. 5, 2004 and identified as ATCC BAA-934. The unencapsulated strain of the trivalent vaccine of the invention, being adherent, is therefore not the unencapsulated strain ATCC 55804. Because the trivalent vaccine of the invention encompasses adherent unencapsulated cells together with cells of strains expressing Type 5 and Type 8 capsular antigens, the trivalent vaccine of the invention has the property of being an effective vaccine for preventing and treating mastitis. Thus, the vaccine of the invention comprises three types of cells, cell lysates, or cell derivatives of Staphylococcus aureus: (1) a type which expresses S. aureus Type 5 capsular antigen, (2) a type which expresses S. aureus Type 8 capsular antigen, and (3) a type which is unencapsulated, which adheres to epithelial cells, which carries an antigen that specifically binds with antibodies to S. aureus Type 336, and which is not a cell, cell lysate, or cell derivative identified as a ATCC 55804, and a pharmaceutically and/or veterinarally acceptable carrier, diluent, excipient, and/or adjuvant.

The cells of this invention can be used as immunogens in vaccines for vaccination against S. aureus. The vaccines can be used to prevent or reduce susceptibility to diseases caused by S. aureus. While the vaccine is effective for eliciting antibody production in a variety of animals, such as bovine, ovine and caprine animals, the vaccine is particularly preferred for the treatment of bovine animals.

The inventive vaccine is a killed cell preparation comprising a mixture of three cell types. Propagation of the three cell types comprising the vaccine in preparation for inactivation by formalin may be accomplished using conventional techniques and culture media known in the art. A variety of both solid and liquid culture media may be suitable for use herein. Following culture on solid media, the cells may be harvested by suspension in a small amount of a suitable carrier, such as PBS. When using liquid culture media, the cells may be optionally concentrated, for example, by filtration or centrifugation to obtain a high density suspension of cells.

Following inactivation, the killed cells of the vaccine can be mixed, conjugated or fused with other antigens, including B or T cell epitopes of other antigens. In formulating the vaccine compositions with the cells, alone or in the various combinations described, the immunogen is adjusted to an appropriate concentration and formulated in a pharmaceutically and/or veterinarally acceptable carrier, diluent, excipient, and/or with any suitable vaccine adjuvant and/or vaccine stabilizer. Typical pharmaceutically acceptable carriers are physiological saline, mineral oil, vegetable oils, aqueous sodium caroboxymethyl cellulose, or aqueous polyvinylppyrrolidone. Typical stabilizers are, for example, sucrose, an alkali metal hydrogen phosphate salt, glutamate, serum albumin, gelatin, or casein. The stabilizer may be any one or more of the foregoing. Suitable adjuvants include, but are not limited to: surface active substances, e.g., hexadecylamine, octadecylamine, octadecyl amino acid esters, lysolecithin, dimethyl-dioctadecylammonium bromide, methoxyhexadecylgylcerol, and pluronic polyols; polyamines, e.g., pyran, dextran-sulfate, poly IC, carbopol; peptides, e.g., muramyl dipeptide, dimethylglycine, tuftsin; oil emulsions; and mineral gels, e.g., aluminum hydroxide, aluminum phosphate, etc. and immune stimulating complexes. The adjuvant may be, for example, alum or a composition containing a vegetable oil, isomannide monooleate and aluminum mono-stearate. Other preferred adjuvants include microparticles or beads of biocompatible matrix materials. The killed cells may be incorporated into microparticles or microcapsules to prolong the exposure of the antigenic material to the subject animal and hence protect the animal against infection for long periods of time. The immunogen may also be incorporated into liposomes, or conjugated to polysaccharides and/or other polymers for use in a vaccine formulation.

Also part of this invention is a composition that comprises the cells of this invention; and a carrier, preferably a biologically-acceptable carrier, and more preferably a pharmaceutically-acceptable carrier. Typical carriers are aqueous carriers such as water, buffered aqueous solutions, aqueous alcoholic mixtures, and the like. Compositions comprising carriers that are for pharmaceutical use, particularly for use in humans, comprise a carrier that is pharmaceutically-acceptable. Examples of such carriers are known in the art and need therefore not be provided herein.

Typically, such vaccines are prepared as injectables: either as liquid solutions or suspensions, solid forms suitable for solution in, or suspension in, liquid prior to injection may also be prepared. The vaccine may be administered to a target animal by any convenient route, such as subcutaneously, intraperitoneally, intramuscularly, intradermally, intravenously, orally, intranasally, or intramammarily, in the presence of a physiologically acceptable diluent. The antigens may be administered in a single dose or in a plurality of doses. The vaccine of the present invention may be stored under refrigeration or in frozen or lyophilized form. The vaccine is administered to the target animal in an amount effective to elicit a protective immune response against S. aureus as compared to a control. The effective amount will vary with the particular target animal, its age and size, and may be readily determined by the practitioner skilled in the art. Suitable regimes for initial administration and booster shots will also be variable, but may be typified by an initial administration followed by subsequent inoculations or other administrations. Further, the vaccine of the invention may be combined with vaccines of other genera of bacteria to provide a single broad spectrum vaccine.

The antigens of the present invention are used to immunize animals against S. aureus. While the vaccine is effective for eliciting antibody production in a variety of animals, the vaccine is particularly preferred for the treatment of bovine animals.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, humanized, CDR-grafted, and single chain antibodies, and the like. Fragments of immunoglobulins, include Fab fragments and fragments produced by an expression library, including phage display. See, e.g., Paul, Fundamental Immunology, Third Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988) Antibodies, A Laboratory Manual, Cold Spring Harbor Publications, New York, for a description of immunoassay formats and conditions that can be used to determine specific immuno-reactivity. Typically a specific or selective reaction will be at least twice background signal to noise and more typically more than 10 to 100 times background.

The vaccine of this invention can be used as immunogens to generate antibodies that are selectively specific for strains of S. aureus. Thus, the vaccine can be used to generate monoclonal and polyclonal antibodies.

To prepare antibodies, a host animal is immunized using the cells of the vaccine, individually or together, as the immunogen. The host serum or plasma is collected following an appropriate time interval to provide a composition comprising antibodies reactive with the immunogen. Methods of antibody (polyclonal and monoclonal) production and isolation are well known in the art. See, for example, Harlow et al. 1988, supra. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody.

In another embodiment, the monoclonal antibody of the invention is a chimeric monoclonal antibody or a humanized monoclonal antibody, produced by techniques well-known in the art.

Still part of this invention is a kit that comprises the vaccine of this invention; and instructions for use of the kit. In addition to the above, the kits may also comprise a control, antibodies, and the like, suitable for conducting the different assays referred to above.

EXAMPLES

Having now generally described this invention, the same will be better understood by reference to certain specific examples, which are included herein only to further illustrate the invention and are not intended to limit the scope of the invention as defined by the claims.

Example 1

Preparation of Whole Cell Vaccine

Encapsulated S. aureus ATCC #49521 serotype 5 and ATCC #49525 serotype 8 were each reactivated in trypticase soy broth (TSB) and plated on blood-agar plates (BAP). One colony was transferred from BAP to 10 ml of Columbia Broth and grown overnight at 37° C. The bacteria were killed by adding formalin to a concentration of 1% and letting stand overnight at room temperature. Kill was determined by streaking a BAP with the suspension and incubating overnight at 37° C. The bacteria were pelleted and washed 2× with sterile PBS by centrifuging at 2500 rpm for 10 min. Gentle pipetting was used to resuspend the bacteria between washings. The final pellet was suspended in 10 ml sterile PBS.

Each bacterial suspension was adjusted to an absorbance of 2 by diluting in PBS. The ATCC strains were adjusted to an absorbance of 2 using OD 600. Smith Compact, deposited at the American Type Culture Collection, ATCC, 10801 University Blvd., Manassas, Va. 20110 on Mar. 5, 2004 and identified as S. aureus strain ATCC BAA-934, was adjusted to an absorbance of 2 using OD 620. Two times the volume of each suspension need to produce an absorbance of 2 was added dropwise to an equal volume of 1% ALHYDROGEL® (Accurate Chemical #1090BS). The mixture was rotated for 30 mm and stored at 4° C. until used.

Example 2

In vitro Phagocytosis Assays

Phagocytosis was determined by flow cytometry according to Saad and Hageltorn with minor modifications (1985. *Acta Vet. Scand.* 26: 289–307). FITC-labeled *S. aureus* was incubated with various sera or Hanks Balanced Salt Solution (HBSS) for 30 min at 37° C. with gentle rocking. Isolated neutrophils ($10 \times 10^6$/ml) were added, and the tubes were incubated for an additional 30 min at 37° C. with gentle rocking. Phagocytosis was stopped by adding 1.0 ml of ice-cold 0.85% saline with 0.04% EDTA. The samples were analyzed by flow cytometry using an EPICS Profile flow cytometer (Coulter Electronics) equipped with a 488 nm argon ion laser. After gating on the appropriate cell population, the percentage of fluorescing cells was recorded. The ingested *S. aureus* were differentiated from the adhered by quenching extracellular fluorescence with 400 µl of 1% methylene blue.

Example 3

Adhesion Assays

Secretory epithelial cells ($10^6$ cells) were plated on rat-tail collagen-coated 60 mm dishes in 5 ml growth medium and grown to confluence by incubating at 37° C. in 5% $CO_2$ for 7 d. The growth medium was replaced every 48 hr. After reaching confluence, the growth medium was removed and 150 µl of NaCl, pooled preimmunization or pooled immune sera, and 3 ml of sonicated *S. aureus* in RPM medium were added to the monolayers and incubated at 37° C. in 5% $CO_2$ for 3 h with rocking. The unadhered *S. aureus* were removed and the monolayers were washed 5 times by holding the dish at an angle and allowing 10 ml of PBS to flow over the monolayer. The monolayers were fixed with methanol and stained with Giemsa (Freshney, R. I. 1987. In: *Culture of Animal Cells. A Manual of Basic Technique*, A. R. Liss, ed. A. R. Liss Inc., New York, N.Y., Page 169). Adhered bacteria in 40 fields of 0.01 mm² were counted microscopically. The assay was performed in triplicate.

Bovine mammary epithelial cells were examined as above for the presence of adherent organisms. The adherence of the 336 positive unencapsulated strain of the vaccine of the invention and the 336 positive unencapsulated strain deposited under ATCC 55804 were compared. The unencapsulated strain used in the current vaccine had an adherence of 165 organisms compared to the unencapsulated ATCC 55804 strain where only 20 organisms adhered.

Example 4

Vaccination of Cows/Immunization Protocols

Ten heifers were vaccinated at approximately 8 weeks before expected parturition. Six similar heifers were unvaccinated controls. The trivalent vaccine was given as a 4 ml dose subcutaneously in the posterior aspect of the left hind limb approximately 50 cm above the hock. Vaccine T1 was given as a 4 ml dose subcutaneously in the same location on the right hind limb.

The same vaccination regimen was repeated adjacent to the respective primary sites at 4 weeks and 2 weeks before calving.

Example 5

Treatment of Cows With Mastitis

Twenty cows that had confirmed cases of *Staphylococcus aureus* mastitis and were considered to be chronic, i.e. at least two successive samplings positive for *S. aureus*, were treated. All cows were immunized with 4 ml of the trivalent vaccine either subcutaneously in the area of the supramammary lymph node or subcutaneously above the shoulder. The cows were immunized on Day 0 of the study then boosted on Day 14 and Day 21. Beginning on Day 15, cows were infused with 10 ml of the antibiotic Pirsue in each quarter following the morning milking. Cows were infused with Pirsue (1x) once a day for 6 days. Sterile quarter milk samples were collected every 30 days and monitored for bacterial growth.

Summarized results are shown in Table 1 and individual cow/quarter results are shown in Table 2. There were 10 cows in each of 2 herds. The vaccine was equally effective in each herd. *Staphylococcus aureus* were cleared in 14 of the 20 cows (70%) and 34 of the 42 infected quarters (81%). Failure to cure selected quarters in some cows could be due to the length time the infections existed. The longer *S. aureus* inhabit the gland, the greater the chance for the formation of abscesses that are impenetrable to antibodies and antibiotics. To insure adequate numbers in each herd, treatment with Pirsue alone was not used since studies in our laboratory and others (Sears and Belschner. 1999. *Proc. Natl. Mastitis Council*, Madison, Wis., Pages 86–92; Sears et al. 2001. *Proceedings of 2nd International Symposium on Mastitis and Milk Quality in Vancouver*, BC, Canada, Pages 13–15) have shown that Pirsue is not effective in curing chronic *S. aureus* infections.

TABLE 1

Effect of vaccine on established *Staphylococcus aureus* infections.

|  | Number Infected | Number Cured | % Cured |
| --- | --- | --- | --- |
| Cows | 20 | 14 | 70 |
| Quarters | 42 | 34 | 81 |

TABLE 2

Effect of vaccine on established *Staphylococcus aureus* infections-individual cow results

| Cow | Herd | *S. aureus* Positive Quarters | 240 days Post Treatment |
| --- | --- | --- | --- |
| 67 | I | LF | negative |
| 1634 | I | LF, RF, LR, RR | positive RR |
| 1800 | I | LF | negative |
| 1803 | I | LR | negative |
| 1840 | I | LF | negative |
| 1845 | I | RF, RR | positive RR |
| 2035 | I | LF, RR | negative |
| 1836 | I | RF, RR | positive LR |
| 1839 | I | RF, RR | positive RF |
| 2042 | I | RF, RR | negative |
| 2722 | II | RF, RR | negative |
| 2763 | II | LF, LR | negative |
| 2598 | II | LF, RF, RR | positive LF, RR |
| 2561 | II | LF, RF, LR, RR | negative |
| 2953 | II | LF, RF, LR, RR | positive LF, RF, RR |
| 2735 | II | LF, RF, LR | negative |
| 2765 | II | LF | negative |
| 2942 | II | LF, RF, RR | negative |
| 2793 | II | LF | negative |
| 2690 | II | RF | negative |

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A vaccine composition comprising (a) cells or cell lysates of a Type 5 *Staphylococcus aureus* strain wherein the cells express *S. aureus* Type 5 capsular antigen, (b) cells or cell lysates of a Type 8 *S. aureus* strain wherein the cells express *S. aureus* Type 8 capsular antigen, and (c) cells or cell lysates of an unencapsulated *S. aureus* strain, identified as ATCC BAA-934, wherein the cells of said unencapsulated strain adhere to epithelial cells and carry an antigen that specifically binds with antibodies to *S. aureus* Type 336, and wherein the cells of said unencapsulated strain are not cells of *S. aureus* strain identified as ATCC55804, and a pharmaceutically or veterinarally acceptable carrier, diluent or excipient, and/or adjuvant.

2. The vaccine composition of claim 1, wherein the cells are formalin-killed.

3. The vaccine composition as claimed in claim 2 comprising an amount of the cells or the cell lysates of said three *S. aureus* strains effective to elicit an immune response specific for *S. aureus* in an animal.

4. The vaccine composition as claimed in claim 2 comprising an amount of the cells or the cell lysates of said three *S. aureus* strains effective to treat *S. aureus*-induced mastitis in an animal.

5. A method of treating *S. aureus*-induced mastitis in an animal comprising administering to said animal the vaccine composition of claim 2 in an amount effective to treat said mastitis in said animal.

6. A method for immunizing an animal against *S. aureus* comprising administering the vaccine composition of claim 2 to said animal in an amount effective to elicit an immune response specific for *S. aureus* in said animal.

7. The method of claim 5 or claim 6, wherein the animal is a bovine animal, a caprine animal, or an ovine animal.

* * * * *